(12) United States Patent
Saiki

(10) Patent No.: US 9,597,460 B2
(45) Date of Patent: *Mar. 21, 2017

(54) DRIVE MECHANISM FOR A DRUG DELIVERY DEVICE

(71) Applicant: SANOFI-AVENTIS DEUTSCHLAND GMBH, Frankfurt am Main (DE)

(72) Inventor: Masaru Saiki, Yamanashi-ken (JP)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/168,571

(22) Filed: May 31, 2016

(65) Prior Publication Data
US 2016/0271333 A1    Sep. 22, 2016

Related U.S. Application Data

(63) Continuation of application No. 14/858,103, filed on Sep. 18, 2015, which is a continuation of application (Continued)

(30) Foreign Application Priority Data

Oct. 4, 2004 (EP) .................................... 04023630

(51) Int. Cl.
*A61M 5/315* (2006.01)
*A61M 5/24* (2006.01)

(52) U.S. Cl.
CPC ...... *A61M 5/31551* (2013.01); *A61M 5/3158* (2013.01); *A61M 5/31501* (2013.01);
(Continued)

(58) Field of Classification Search
CPC .......... A61M 5/31511; A61M 5/31551; A61M 2207/00; A61M 5/24; A61M 5/31558;
(Continued)

(56) References Cited

U.S. PATENT DOCUMENTS 533,575 A    2/1895  Wilkens
3,481,022 A  12/1969 Neuschotz
(Continued)

FOREIGN PATENT DOCUMENTS

CN   1441684 A    9/2003
DE   19900792 C1  6/2000
(Continued)

OTHER PUBLICATIONS

European Examination Report for EP App. No. 05786310.2, dated Dec. 8, 2009.
(Continued)

*Primary Examiner* — Bhisma Mehta
*Assistant Examiner* — Brandy S Lee
(74) *Attorney, Agent, or Firm* — McDonnell Boehnen Hulbert & Berghoff LLP

(57) ABSTRACT

A drive mechanism for a drug delivery device having a rotationally fixed plunger rod driven by a lead screw. The lead screw engages a free lock which is coupled to a release knob. A dose setting dial cooperates with an inner cylinder using a clutch to establish the axial movement of the plunger rod during dose setting and dispensing.

20 Claims, 9 Drawing Sheets

Related U.S. Application Data

No. 14/844,264, filed on Sep. 3, 2015, which is a continuation-in-part of application No. 12/195,033, filed on Aug. 20, 2008, now Pat. No. 9,155,841, which is a continuation-in-part of application No. 11/690,995, filed on Mar. 26, 2007, now abandoned, which is a continuation of application No. PCT/EP2005/009839, filed on Sep. 14, 2005.

(52) U.S. Cl.
CPC .... *A61M 5/31511* (2013.01); *A61M 5/31528* (2013.01); *A61M 5/31585* (2013.01); *A61M 5/24* (2013.01); *A61M 5/31558* (2013.01); *A61M 5/31575* (2013.01); *A61M 5/31586* (2013.01); *A61M 2202/0478* (2013.01); *A61M 2207/00* (2013.01)

(58) Field of Classification Search
CPC ............ A61M 5/31575; A61M 5/3158; A61M 5/31585; A61M 5/31586; A61M 29/02; A61M 2202/0478; A61M 5/31501; A61M 5/31528
See application file for complete search history.

(56) References Cited

U.S. PATENT DOCUMENTS

| | | | |
|---|---|---|---|
| 3,891,127 A | 6/1975 | Fernandez et al. | |
| 4,498,904 A | 2/1985 | Turner et al. | |
| 5,226,895 A | 7/1993 | Harris | |
| 5,279,585 A | 1/1994 | Balkwill | |
| 5,279,586 A | 1/1994 | Balkwill | |
| 5,304,152 A | 4/1994 | Sams | |
| 5,308,340 A | 5/1994 | Harris | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,545,147 A | 8/1996 | Harris | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,820,602 A | 10/1998 | Kovelman et al. | |
| 5,921,966 A | 7/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 * | 4/2001 | Burroughs ........ | A61M 5/31551 604/153 |
| 6,235,004 B1 * | 5/2001 | Steenfeldt-Jensen | A61M 5/31551 604/207 |
| 6,248,095 B1 | 6/2001 | Giambattista et al. | |
| 6,699,224 B2 | 3/2004 | Kirchhofer et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 9,155,841 B2 | 10/2015 | Saiki | |
| 2002/0052578 A1 | 5/2002 | Moller | |
| 2002/0120235 A1 | 8/2002 | Enggaard | |
| 2002/0165500 A1 | 11/2002 | Bechtold et al. | |
| 2003/0050609 A1 | 3/2003 | Sams | |
| 2004/0059299 A1 | 3/2004 | Moller | |
| 2004/0199117 A1 | 10/2004 | Giambattista et al. | |
| 2004/0210199 A1 | 10/2004 | Atterbury et al. | |
| 2004/0210298 A1 | 10/2004 | Rabkin et al. | |
| 2007/0244436 A1 | 10/2007 | Saiki | |
| 2010/0069845 A1 | 3/2010 | Marshall et al. | |

FOREIGN PATENT DOCUMENTS

| | | |
|---|---|---|
| EP | 0937471 | 8/1999 |
| EP | 0937476 | 8/1999 |
| EP | 1799287 B1 | 6/2013 |
| RU | 2091087 C1 | 9/1997 |
| RU | 2212254 C2 | 9/2003 |
| WO | 91/14467 | 10/1991 |
| WO | 93/07922 A1 | 4/1993 |
| WO | 98/10813 | 3/1998 |
| WO | 99/38554 | 8/1999 |
| WO | 01/10484 | 2/2001 |
| WO | 01/87386 | 11/2001 |
| WO | 01/95959 | 12/2001 |
| WO | 2006/037435 | 4/2006 |
| WO | 2013/137893 | 9/2013 |

OTHER PUBLICATIONS

Chinese Office Action for CN App. No. 200580033832.2, issued Sep. 26, 2008.
Russian Decision of Grant for RU App. No. 2007116817, Oct. 5, 2009.
Russian Office Action for RU App. No. 2007116817, dated Jul. 7, 2009.
International Preliminary Report on Patentability for Int. App. No. PCT/EP2005/009839, completed Feb. 5, 2007.
International Search Report for Int. App. No. PCT/EP2005/009839, completed Dec. 20, 2005.

\* cited by examiner

DRIVE MECHANISM FOR A DRUG DELIVERY DEVICE

CROSS REFERENCE TO RELATED APPLICATIONS

The present application is a continuation of U.S. patent application Ser. No. 14/858,103, filed Sep. 18, 2015, which is a continuation of U.S. patent application Ser. No. 14/844,264, filed Sep. 3, 2015, which is a continuation of U.S. patent application Ser. No. 12/195,033, filed Aug. 20, 2008, now U.S. Pat. No. 9,155,841, which is a continuation of U.S. patent application Ser. No. 11/690,995, filed Mar. 26, 2007, which is a continuation of PCT/EP2005/009839, filed Sep. 14, 2005, which claims priority to European Patent Application No. 04023630.9, filed Oct. 4, 2004. The entire disclosure contents of these applications are herewith incorporated by reference into the present application.

FIELD OF THE INVENTION

This invention relates to a drive mechanism for a drug delivery device that allows the user to select multiple doses of an injectable drug and for the dispensing of the set dosage of the drug and applying said drug to a patient, preferably by injection. In particular, the present invention relates to such devices, which are handled by the patients themselves.

BACKGROUND

Drug delivery devices, which allow multiple dosing of the required dosage of liquid drug and administration of the liquid to a patient, are well known in the art. Generally, such devices have substantially the same purpose as that of an ordinary syringe.

Injectors of this kind must meet a number of requirements to meet user needs. These devices need to be robust in construction, yet easy to use both in terms of the manipulation of the parts and understanding by a user of its operation. In the case of those with diabetes, many users will be physically infirm and may also have impaired vision. Where the injector is to be disposable rather than reusable, the injector should be cheap to manufacture and easy to dispose of (preferably being suitable for recycling).

WO 9114467 A1 discloses a dispensing device, comprising a drive mechanism having a telescopic piston rod consisting of a first and a second threaded member having equi-spaced threaded segments with non-threaded segments therebetween. The device further comprises a dose setting sleeve, which surrounds the second threaded member being coupled for rotation and is threadedly engaged with the device shell. The threads of the three said components are of the same lead. The design of this device requires a body length to plunger length ratio of about 1:1 in order to allow dispensing of relatively large doses. However, simple and safe correction of a set overdose by the patient remains unresolved without either dispensing the set amount of fluid or dismantling the cartridge.

WO 9938554 A2 teaches an injection syringe for apportioning set doses of a medicine from a cartridge wherein a drive mechanism comprising a unidirectional coupling (ratchet) is disclosed which allows correction of a set overdose without dispensing a set amount of fluid or requiring the dismantling of the cartridge. The device is further designed so that an initial reluctance has to be overcome before the unidirectional coupling can be rotated during dose dispensing.

WO 0195959 A1 discloses an injection device for injection of set doses of medicine from a cartridge, in which syringe a dose is set by screwing a nut up along a threaded piston rod, whereby a dose setting drum, which carries on its cylindrical surface along a helix a scale of which a number corresponding to the set dose is shown in a window in the housing of the syringe, and an injection button, which is elevated over the end of the syringe, are moved axially a distance which is larger than the axial movement of the nut. A gear wheel transmission is established between the nut and the injection button such that the gearing makes the movement of the button larger and the force, which has to be exerted on the injection button, is correspondingly reduced.

Accordingly, the problem to be solved by the instant invention is to reduce the actuation (injection) force required during drug dispensing especially when dispensing large doses whilst maintaining a compact design and thereby improving user handling, and providing the user with a means to intuitively, safely and easily correct a set dose.

SUMMARY

Therefore, it is an object of the present invention to provide an alternative drive mechanism to existing technologies suitable for the efficient transmission of an actuation force in drug delivery devices, particularly compact devices, e.g., of pen-type shape, which additionally allows the dispensing of large doses of drug and which further provides the advantage of intuitive and easy to use correction of a set dose.

BRIEF DESCRIPTION OF THE FIGURES

FIG. 1 is a perspective view of the entire device.

FIG. 2 is a sectional side view showing the drive mechanism of the device in an initial state.

FIG. 3 is a sectional side view illustrating a dose setting operation of the device.

FIG. 4 is a sectional side view illustrating a dose delivery of the device.

FIG. 5 is an enlarged scale of FIG. 2.

FIG. 6 shows the plunger rod, the lead screw, and the plunger rod holder of the device.

DETAILED DESCRIPTION

Figure 1:
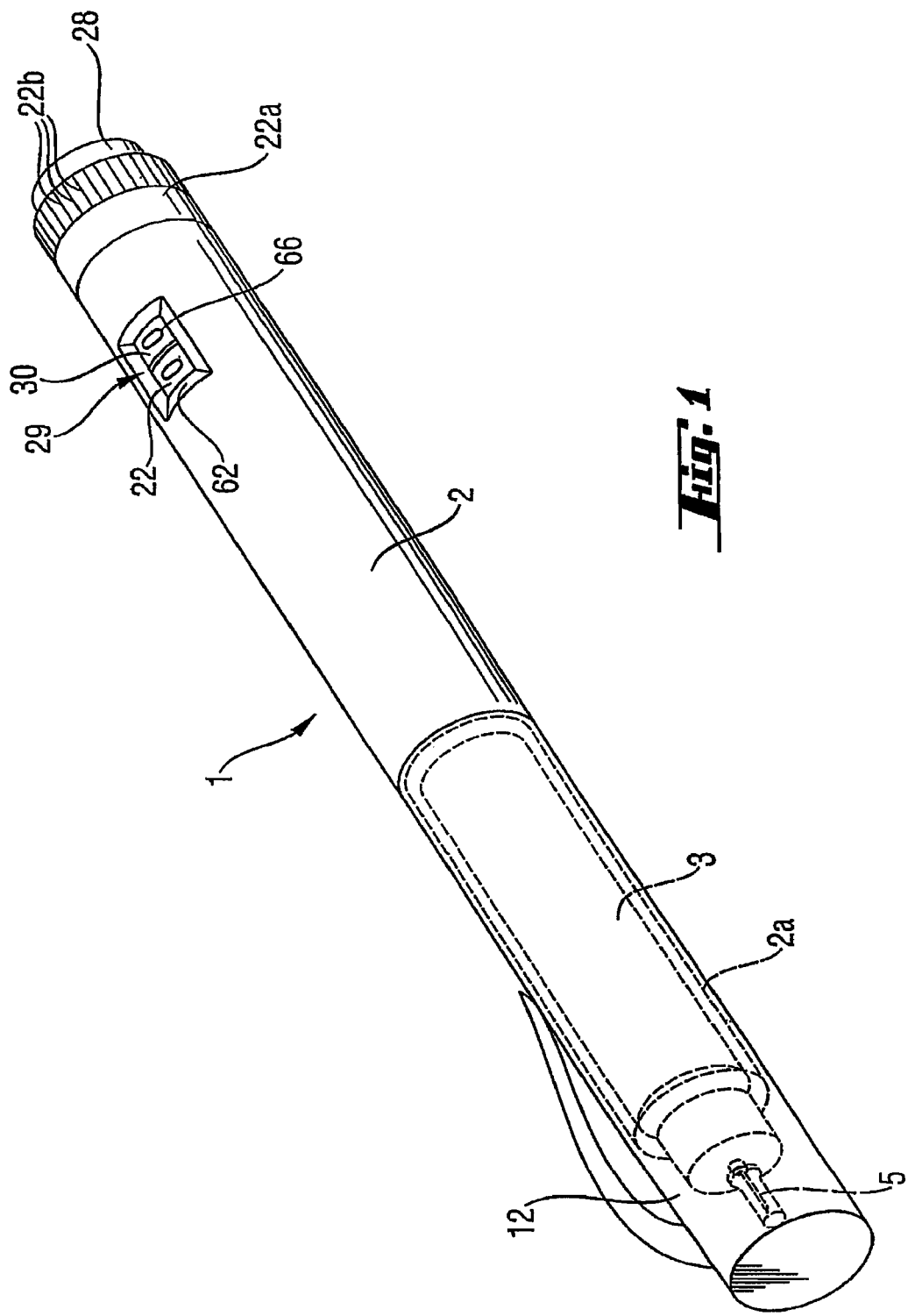
FIGS. 1 to 6 relate to the drug delivery device of embodiment 1, FIGS. 7 to 8 relate to the drug delivery device of embodiment 2 to which the present invention is applied.

A first aspect of the instant invention is to provide a drive mechanism for a drug delivery device comprising:

a plunger rod having a non-circular cross section and being hollow, said plunger rod being prevented from rotation;

a lead screw engaged with said plunger rod;

a dose setting dial rotatably moving towards the proximal end during dose setting and rotatably moving towards the distal end during dose dispensing;

an inner cylinder being releasably connected to the dose setting dial, such that relative rotation between said dose setting dial and said inner cylinder is prevented during dose setting but is allowed during dose dispensing; and a plunger rod holder, which prevents said plunger rod from moving towards the proximal end during dose setting, but allows said plunger rod to move towards the distal end during dose dispensing;

optionally further comprising a free lock.

A second aspect of the instant invention is a drug delivery device comprising the drive mechanism according to the invention.

A third aspect of the instant invention is the use of a drive mechanism according to the invention in a method of assembling a device according to the invention.

A fourth aspect of the instant invention is the use of a drive mechanism or a device according to the invention for the administration of a pharmaceutical formulation to the human or animal body.

Another aspect of the instant invention is a method of assembling a drug delivery device according to the invention, comprising the step of mounting the mechanism according to the invention to any components in order to assemble a drug delivery device.

The terms, which are used in order to define the instant invention, are generally to be understood in accordance with the general knowledge of the person skilled in the art. Further, the following terms shall have the following, optionally preferred, meaning in accordance with the instant invention:

The term "drug delivery device" according to the instant invent on shall mean a multi-dose, disposable, mobile, hand-held device designed to dispense a selected dose of medicament, e.g. insulin, insulin analogues, growth hormones, low molecular heparins, and their derivatives etc., optionally suitable for self-administration. Said device is of the mechanical pen-type. Preferably, the term "drug delivery device" shall mean a disposable, multi-dose, pen-type device having mechanical dose delivery and dose selection mechanisms designed for regular injection by persons without formal medical training, e.g., patients. Usually, the "drug delivery device" of the instant invention comprises a cartridge, which contains a pharmaceutical formulation, which can be administered via a needle, and, optionally a cartridge holder.

The term "pharmaceutical formulation" shall preferably mean a liquid or suspension or the like contained in the cartridge, comprising a drug or vaccine. The drug may contain one or more proteins, peptides, or small molecules, which may be administered subcutaneously. Preferably, the drug is one or more hormone or antithrombotic, especially selected from the group consisting of insulins, heparins, derivatives, analogous, and substitutes thereof.

The term "housing" according to the instant invention shall preferably mean an exterior or interior ("insert") cover. The housing may be designed to enable the safe, correct, and comfortable handling of the drug delivery device (e.g., the drive mechanism). Usually, it is designed to house, fix, protect, guide, and/or engage with the inner mechanism(s) or components of the drug delivery device (e.g., the drive mechanism) by limiting the exposure to contaminants, such as liquid, dust, dirt etc. In general, the housing may be unitary or a multipart component of tubular or non-tubular shape. Preferably, the "housing" is designed to contain a cartridge and optionally a cartridge holder, which is preferably mounted at the distal end of the housing.

The term "engaged" according to the instant invention shall mean the interlocking of two or more components of the drive mechanism/drug delivery device, preferably the interlocking of screw structures of components.

The term "screw structure" according to the instant invention shall mean a full or part thread, e.g., a cylindrical spiral rib/groove located on the internal and/or external surface of a component of the drug delivery device, having an essentially triangular or square or rounded section designed to allow continuous free rotational and/or axial movement between components. Optionally, a screw structure may be further designed to prevent rotational or axial movement of certain components in one direction. Screw structures are incorporated between the threaded insert and the dose setting dial (hereinafter the "first screw structure"), between the inner cylinder and the free lock (hereinafter the "second screw structure"), and between the lead screw and the plunger rod (hereinafter the "third screw structure"). The said screw structures according to instant invention shall preferably have different screw pitches to allow force transmission from the proximal end to the distal end during dose delivery. Therefore, the screw pitch ratios between the $1^{st}$ $2^{nd}$ and $3^{rd}$ screw structures are about 1.8-4.2:1.8-4.2:1, preferably about 2.4-3.6:2.4-3.6:1.

It is further preferred, that the screw pitches of the $1^{st}$ screw structure and the $2^{nd}$ screw structure are the same.

The term "dose setting dial" according to the instant invention shall preferably mean an essentially tubular component of essentially circular cross-section having an external thread engaged with the housing by means of a first screw structure, allowing the dose setting dial to rotatably move towards the proximal end during dose setting and rotatably move towards the distal end during dose dispensing. The "dose setting dial" according to the instant invention is designed to indicate a selected dose of the dispensable product (e.g., a drug). This may be achieved by use of markings, symbols, numerals, etc., e.g. printed on the external surface of the dose setting dial or an odometer, or the like.

Additionally, the dose setting dial is releasably connected to the inner cylinder by a clutch means. To set the dose, the dose setting dial is rotated and the dose setting dial and the inner cylinder rotate together towards the proximal end. During dose dispensing, the clutch means disengages the dose setting dial from the inner cylinder, such that the dose setting dial rotates relative to the inner cylinder towards the distal end. Further, the dose setting dial may comprise one or more stops to limit the maximum amount of a single dose.

The term "inner cylinder" according to the instant invention shall mean any essentially tubular component of essentially circular cross-section, which is releasably connected to the dose setting dial, such that relative rotation between said dose setting dial and said inner cylinder is prevented during dose setting but is allowed during dose dispensing. In a preferred embodiment the inner cylinder is further engaged with the lead screw by a free lock. In another preferred embodiment the inner cylinder is further engaged with the piston rod in order to allow the lead screw to rotate with the inner cylinder during dose setting, e.g., by means of splined projections located in a key way in the inner surface of the inner cylinder. During dose dispensing the inner cylinder is disengaged from the dose setting dial by a clutch means and is moved towards the distal end without rotation (with respect to the housing).

The term "releasably connected" according to the instant invention shall mean that two components of the instant mechanism or device are reversibly joined with each other, allowing coupling and decoupling. This is achieved, e.g., by a clutch means.

The term "plunger rod" according to the instant invention shall mean any component adapted to operate through/within the housing, designed to transfer forces from the proximal end to the distal end of the drug delivery device, preferably to the cartridge piston, for the purpose of drug dispensing. According to the instant invention, the "plunger rod" is essentially cylindrical, hollow, and has a non-circular cross-section. The "plunger rod" is a component of the drive mechanism, which is prevented from rotation with respect to the housing by means of the plunger rod holder. The "plunger rod" abuts the cartridge piston at the distal end of the plunger rod. In a particular embodiment, the "plunger rod" has ratchet teeth or the like which interact with the plunger rod holder.

The term "plunger rod holder" according to the instant invention shall mean any component, which prevents movement of the plunger rod towards the proximal end during dose setting, but allows movement of the plunger rod towards the distal end during dose dispensing. Optionally, the plunger rod is also prevented from rotation by the plunger rod holder. In order to achieve the aforementioned, the plunger rod holder engages with the plunger rod, e.g., by means of ratchet teeth and ratchet teeth arms.

The plunger rod holder may be a separate component or be an integral part of the housing or any other component. Furthermore, there are many other suitable solutions within the knowledge of the person skilled in the art in order to essentially prevent the plunger rod from movement in the proximal direction.

The term "distal end" according to the instant invention shall mean the end of the device or a component of the device, which is closest to the dispensing end of the device.

The term "proximal end" according to the instant invention shall mean the end of the device or a component of the device, which is furthest away from the dispensing end of the device.

The term "clutch means" according to the instant invention shall mean any means, which releasably connects the dose setting dial and the inner cylinder and which is designed to allow rotation of the dose setting dial and the inner cylinder with respect to the housing when the dose setting dial and the inner cylinder are coupled and, when both are de-coupled, allows rotation of the dose setting dial with respect to the housing, but does not allow rotation of the inner cylinder with respect to the housing and allows axial movement of the inner cylinder. Accordingly, the term "clutch means" is any clutch engaging for the purpose of reversibly locking two components in rotation, e.g., by use of axial forces to engage a set of face teeth (saw teeth, dog teeth, crown teeth) or any other suitable frictional faces.

The term "periphery" according to the instant invention shall usually mean the surface of any part, preferably the surface along the longitudinal axis.

The term "original position" according to the instant invention shall mean the starting position of the dose setting dial, i.e., when the set amount of dosage is zero ("00"). This is usually the case, when the device has not yet been used, a full cartridge has been loaded, or the device is in use and the set amount of drug has been completely expelled, respectively, dispensed.

The term "lead screw" according to the instant invention shall mean any essentially cylindrical component, which is engaged with the plunger rod, preferably threadedly engaged, and rotates with respect to the plunger rod when moving towards the proximal direction during dose setting, and moving axially towards the distal end without rotation during dose dispensing. In a preferred embodiment, the lead screw is further engaged with a free lock, (e.g., a friction clutch, a thrust bearing or the like), preferably threadedly engaged.

The term "free lock" shall mean an essentially cylindrical component having both an external and internal thread and being threadedly engaged with the inner cylinder and threadedly engaged with the lead screw. Preferably, during dose setting and dose dispensing, relative rotational movement between a) the free lock and the inner cylinder, and b) the free lock and the lead screw is allowed and relative axial movement between the free lock and the inner cylinder is allowed, whilst relative axial movement between the free lock and the lead screw is restricted.

In a more particular embodiment, the free lock is threadedly engaged between the inner surface of the inner cylinder and the external surface of the lead screw, optionally at the proximal end of the lead screw.

In yet another preferred embodiment, the free lock is fixed to the plunger rod holder, whereby relative axial movement between the free lock and the lead screw is not restricted.

Accordingly, the term "free lock" means a mechanism combining the characteristics of both a clutch mechanism (e.g., a slip clutch) and a force reduction mechanism.

The term "counter ring" according to the instant invention shall mean any constructive element, which is in an interlocking relationship to the dose setting dial. In a preferred embodiment, the counter ring is assembled concentrically on the outer circumference of the dose setting dial, optionally adjacent to the front side of the threaded insert. In another preferred embodiment, a positioning collar is assembled on the outer circumference of the dose setting dial adjacent to the front side of the counter ring, optionally, the cylindrical positioning collar is integrated into the housing.

The "counter ring" shall indicate one digit of the amount of the set dose by means of indices along its outer circumference, whereas one or more further digits of the set dose is indicated by indices along the outer circumference of the dose setting dial.

Preferably, dialing of the "counter ring" shall enable to set the smallest increments of the set dose (e.g., tens, eights, quarters, or halves of a unit, or single units).

The term "interlocking relationship" according to the instant invention shall mean any constructive connection of the counter ring and the dose setting dial, which allows both, the counter ring and the dose setting dial, to rotate together, preferably by means of a screw structure (e.g., thread, groove, rib), and also allows longitudinal axial movement of the dose setting dial with respect to the counter ring, when the dose setting dial is moved (in either forward or backward direction). Preferably, the counter ring remains visible in the display window and displays the set dose (amount of drug), when the dose setting dial is screwed out in order to set the dose.

The term "display window" according to the instant invention shall mean any opening in the housing, e.g. a hole, or a transparent section in the housing, which allows displaying the status of the device, preferably, the status of dose setting, particularly, the amount of set dose. This is preferably achieved, e.g., by means of a dose indicator, which exhibits one or more numerical or graphical symbols or values or characters, preferably two or three digits in order to indicate the set amount of dose. In another preferred embodiment, the "display window" displays the value of the selected amount of dose consisting of one or more digits indicated along the circumference of the outer periphery of the counter ring, and one or more digits indicated along the circumference of the outer periphery of the dose setting dial.

The description and definitions of the various components stated herein are related to exemplified embodiments and should not be considered limiting of the claimed components.

In another embodiment, the display window is preferably located essentially at the proximal end of the device.

According to the drug delivery device of the instant invention, the distal end of the plunger rod abuts the cartridge piston and the proximal end of the plunger rod is engaged with the lead screw. During dose setting, the lead screw is driven to rotate by the inner cylinder towards the proximal end with respect to the plunger. The plunger rod and lead screw are configured in a telescopic-like structure, thereby, reducing the overall length of the drive mechanism.

Further, the plunger rod is engaged with the plunger rod holder, such that rotational movement during both dose setting and dose dispensing is prevented. The plunger rod holder is also designed to prevent linear movement of the plunger rod towards the proximal end during dose setting but allow distal linear movement of the plunger rod during dose dispensing. The mechanism of instant invention allows dose setting to be performed repeatedly with great accuracy.

Proximal axial movement of the plunger rod during dose setting is prevented by the use of ratchet teeth formed along the outer periphery of the plunger rod which engage with a plurality of ratchet teeth arms formed on the plunger rod holder.

Rotational movement of the non-circular cross section plunger rod is prevented by it being inserted in a corresponding non-circular passage way formed in the plunger rod holder.

Embodiment 1 of the present invention is described with reference to the drawings.

Figure 2:
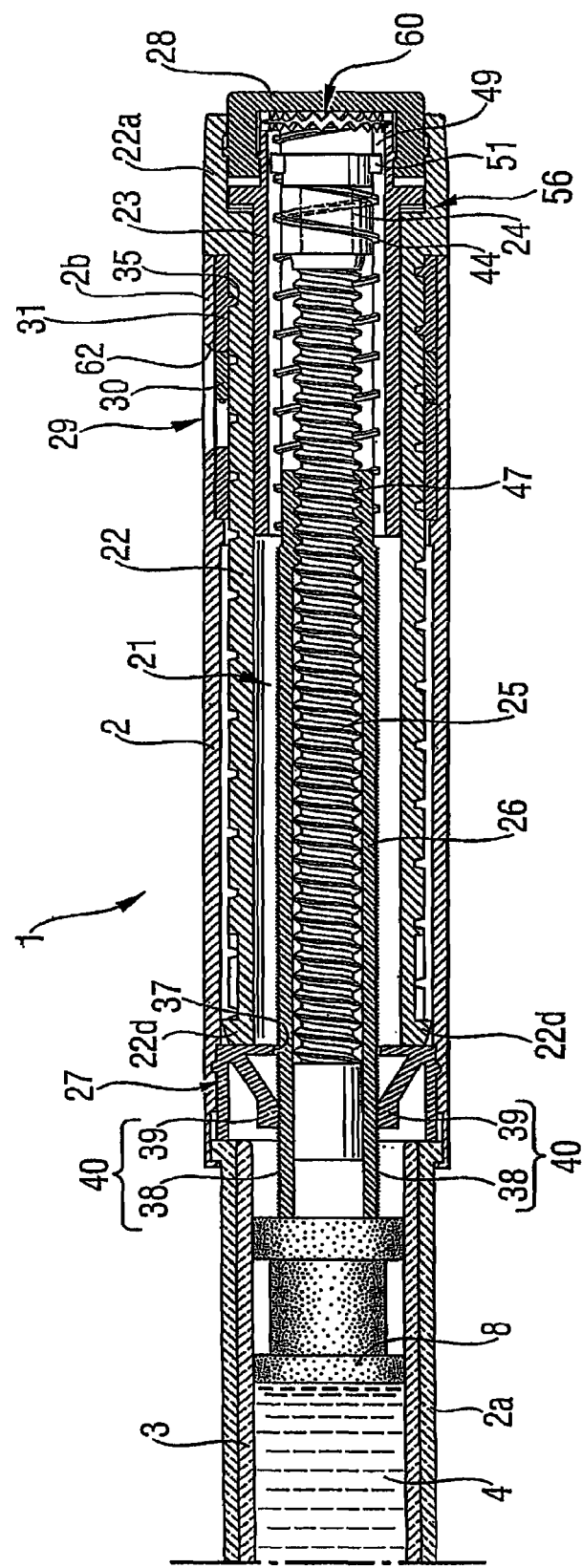
Figure 3:
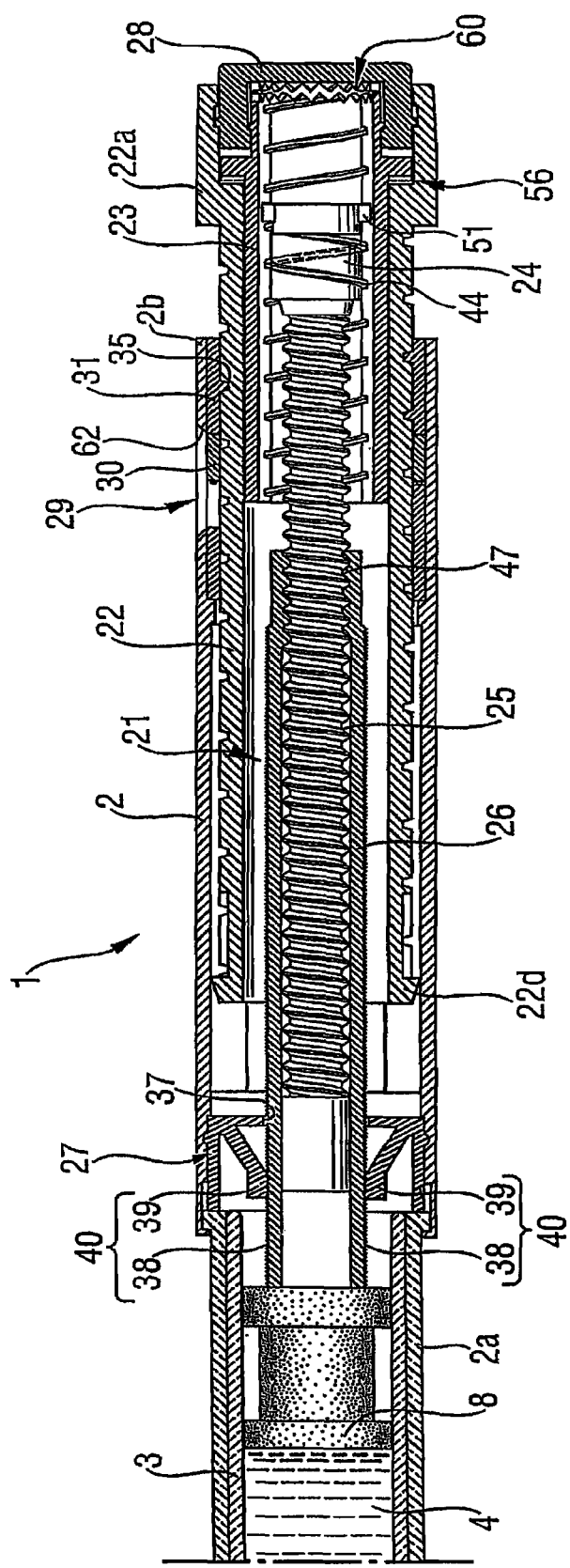
Figure 4:
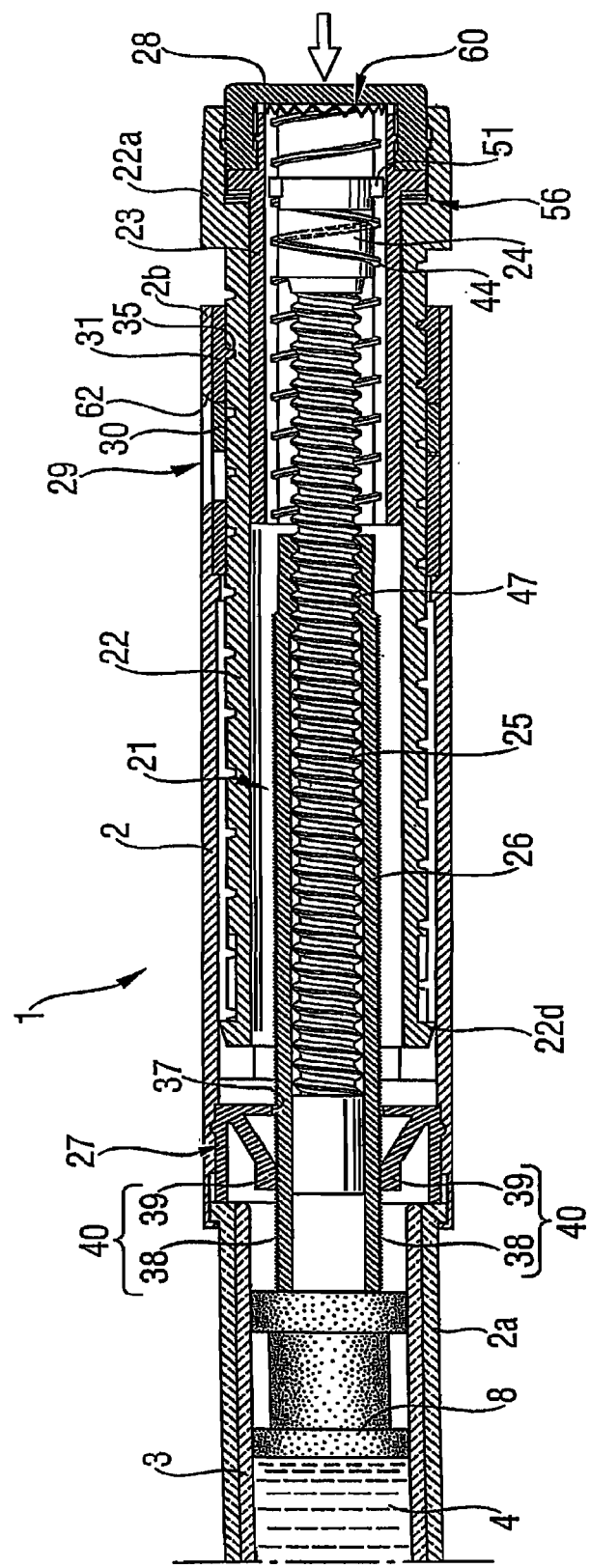
Figure 5:
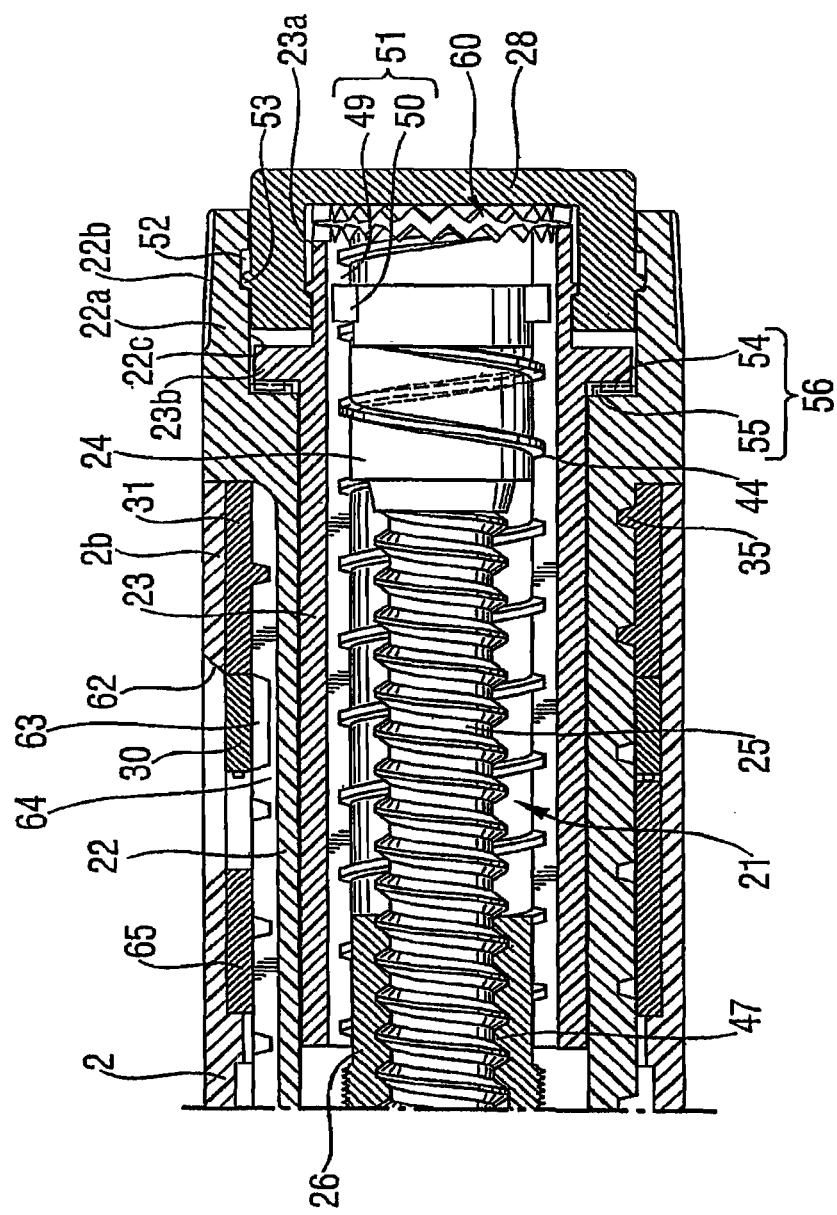
Figure 6:
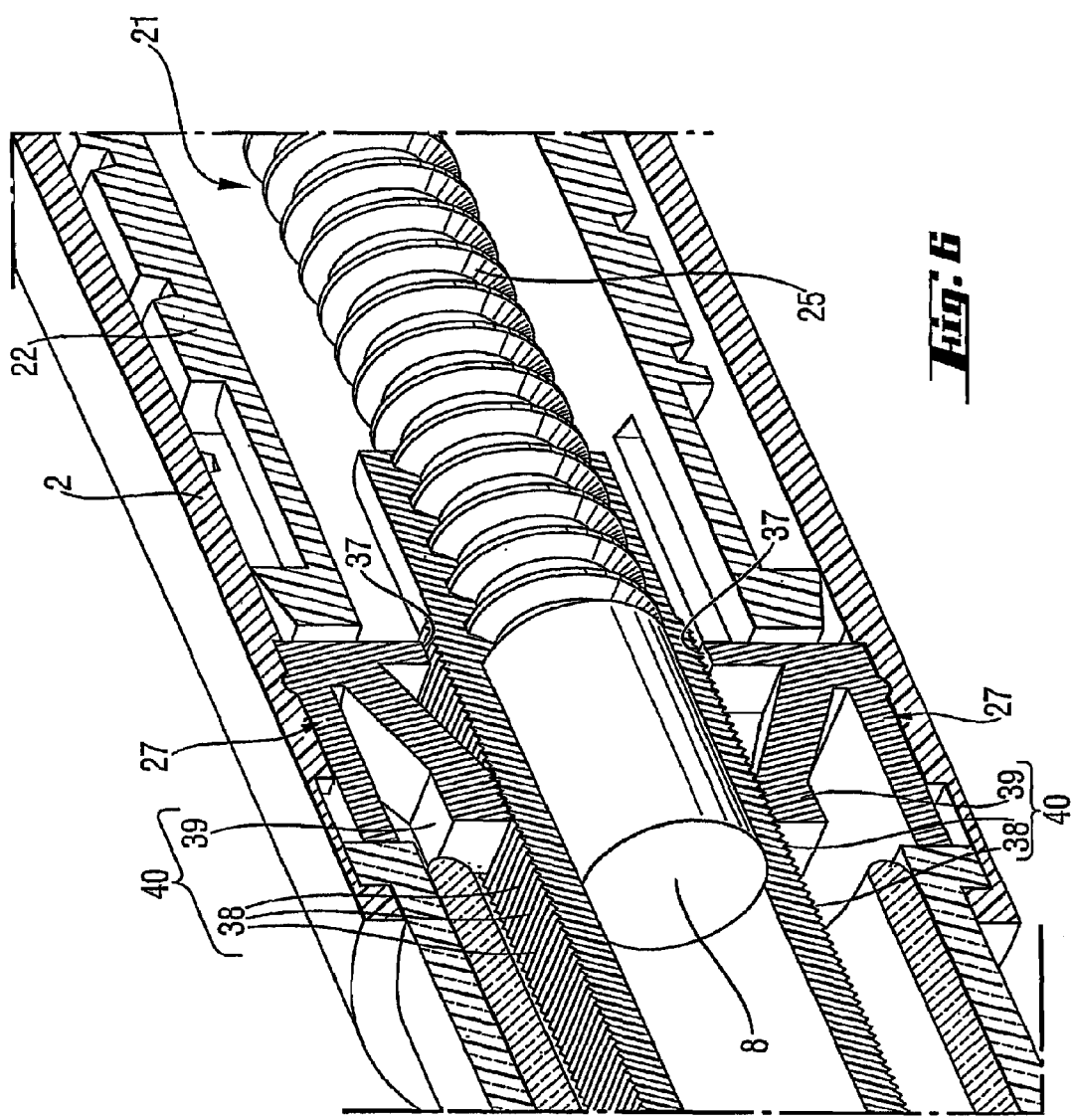

An outline of the device (1) is described with reference to FIGS. 1 to 2.

The device is of the mechanical pen type and consists of:
a housing (2);
a cartridge-holder (2a) coupled to the distal end of the housing (2);
a cartridge (3), sealed by a piston (8) mounted in the proximal end of the cartridge and containing a liquid (4) drug, mounted in the cartridge-holder (2a);
a removable cap (12) attached to the distal end of the device;
a piston driving assembly (21) assembled in the proximal end of the housing (2).

The piston driving assembly transfers an activation force from the proximal end to the distal end during dispensing. The piston driving assembly (21) consists of a dose setting dial (22), an inner cylinder (23), a free lock (24), a lead screw (25), a plunger rod (26), a plunger rod holder (27), a release knob (28), a dose indicator (or counter) (29), a counter ring (30) and a threaded insert (31).

Screw structures are incorporated between the threaded insert (31) and the dose setting dial (22) (i.e., the "first screw structure"), between the inner cylinder (23) and the free lock (24) (i.e., the "second screw structure"), and between the lead screw (25) and the plunger rod (26) (i.e., the "third screw structure").

Operation of the device will now be described. To set a desired dose to be delivered a user rotates the rotating knob (22a) of the dose setting dial (22), thus moving the dose setting dial towards the proximal end by means of the first screw structure (35). During dose setting relative rotation between the dose setting dial (22) and the inner cylinder (23) is prevented by a clutch (56), thus allowing the inner cylinder When the inner cylinder (23) rotates towards the proximal end during dose setting, the lead screw (25) rotates integrally with the inner cylinder (23), with respect to the plunger rod (26), by virtue of a pair of splined projections (50) located in a key way (51) in the inner surface of the inner cylinder (23). When the lead screw (25) rotates out of the plunger rod (26) towards the proximal end, the plunger rod holder (27) locks the plunger rod (26) to prevent the plunger rod from being displaced towards the proximal end thus maintaining the abutment with the piston (8).

The rotation of the inner cylinder (23) further moves the free lock (24) towards the distal end through the second screw structure (44).

The set dose in the current embodiment is indicated by numerical values (66) on the indicator (counter) (29) and the dose setting dial (22) displayed in the display window (62).

To administer a selected dose to a patient, the user depresses the release knob (28) towards the distal end, uncoupling the dose setting dial (22) from the inner cylinder (23) allowing the dose setting dial to rotate relative to the inner cylinder and move towards the distal end. The inner cylinder (23) moves axially towards the distal end thus rotating the free lock (24) in a proximal direction at a predetermined speed-reducing ratio transferring the axial movement of the inner cylinder (23) to the lead screw (25) moving it axially towards the distal end. The lead screw (25) thus pushes the plunger rod (26) towards the distal end. This in turn pushes the piston (8) towards the distal end expelling the contents from the cartridge (3) through the needle (5) into the patient.

Details of the device of embodiment 1 are described with reference to FIGS. 2 to 6.

The threaded insert (31) is concentrically assembled and secured to the inside of the proximal end portion (2b) of the housing (2) by suitable methods known by those skilled in the art. The threaded insert (31) is threadedly engaged with the essentially cylindrically shaped dose setting dial (22) forming the first screw structure (35). The dose setting dial (22) is mounted to allow rotational movement towards the proximal end during dose setting and the distal end during dose delivery. Stops (22d), preferably in the form of a pawl, are formed on the distal end of the dose setting dial (22).

A cylindrical rotating knob (22a) having a diameter equal to the outer diameter of the housing is attached to the proximal end of the dose setting dial (22). Serrations (22b) are formed on the outer surface of the rotating knob (22a) to improve grip for the user.

The inner cylinder (23) is assembled concentrically within the dose setting dial (22) and is releasably connected to the dose setting dial (22) by a clutch means (56). An essentially cylindrically shaped flange portion is formed at the proximal end (23a) of the inner cylinder (23) and inserted into the hollow recess (22c) of the rotating knob (22a).

The outer surface of the free lock (24) is threadedly engaged with the inner surface of the inner cylinder (23) forming the second screw structure (44). The free lock (24) is free to rotate and move axially towards the distal end and the proximal end within the inner cylinder (23).

The inner surface of the free lock (24) is threadedly engaged with the outer surface of the proximal end of the essentially non-circular cross section lead screw (25). The free lock (24) is free to rotate on the outer surface of the lead screw (25) and move axially towards the distal end and the proximal end of the lead screw (25).

The distal end of the lead screw (25) is threadedly engaged with the proximal end of the plunger rod (26) forming the third screw structure (47).

The essentially non-circular cross section, preferably a square tube shape, plunger rod (26) has small pitch ratchet teeth (38) on its outer surface, preferably on two opposing faces of the outer surface.

The plunger rod holder (27) is secured to the inner side of the distal end of the housing (2) by any suitable means known by a person skilled in the art. A square passageway (37), having a dimension equal to the outer diameter of the plunger rod (26) is formed in the centre of the plunger rod holder (27). The plunger rod (26) is engaged with the square passageway (37), such that rotation of the plunger rod (26) is prevented by the plunger rod holder (27).

A plurality of pairs of flexible ratchet teeth arms (39), preferably two, is formed on the plunger rod holder (27). These form the ratchet mechanism (40) of the device. Further embodiments could be envisaged where three or four ratchet teeth arms are formed on the plunger rod holder (27) having, for example, 90° (e.g., 4 arms) or 120° (e.g., 3 arms) offset, or the like.

The ratchet mechanism (40) is engaged with the ratchet teeth (38) of the plunger rod (26) such that axial movement of the plunger rod (26) towards the proximal end is prevented but axial movement of the plunger rod (26) towards the distal end is allowed.

A plurality of spline grooves (49), preferably two, is formed on the inner surface of the inner cylinder (23). A plurality of splined projections (50), preferably two, is formed on the outer surface of the proximal end of the lead screw (25). The splined projections (50) engage with the spline grooves (49) of the inner cylinder (23) permitting axial movement of the lead screw (25) towards the distal end and the proximal end with respect to the inner cylinder (23). The spline grooves (49) and the splined projections (50) together form a splined structure (51).

A release knob (28) of essentially cylindrical shape, open at the distal end and closed at the proximal end, is assembled concentrically in the hollow (22c) on the inner side of the rotating knob (22a). An annular rib (53) is formed on the outer circumference of the release knob (28) and is engaged with an annular groove (52) on the inner circumference of the rotating knob (22a). The release knob (28) is thus free to rotates and move axially towards the distal end and the proximal end with respect to the rotating knob (22a). Movement of the release knob (28) towards the distal end and the proximal end is limited by the width of the annular groove (52).

The release knob (28) moves such that it can be brought in and out of abutment with the flange portion (23b) of the inner cylinder (23).

A wave-shaped annular (54), e.g., as teeth, or the like, is formed on the distal end face of the flange portion (23b) of the inner cylinder (23) and is engaged with a corresponding wave-shaped shoulder (55) on the dose setting dial (22). The wave-shaped annular (54) and the wave-shaped shoulder (55) together form a first clutch (56) releasably connecting the dose setting dial (22) and the inner cylinder (23) such that relative rotational movement is prevented during dose setting.

A second clutch (60) is formed between the proximal end of the inner cylinder (23) and the inner face of the release knob (28). The second clutch (60) consists of two complementary wave-shaped configurations, teeth-shaped configurations, or the like, located on the release knob (28) and the inner cylinder (23).

In the present embodiment the set dose is indicated as a numerical value on the counter ring (30) and the dose setting dial (22). The set dose is viewed through a display window (62) located at the proximal end of the housing (2). The display window (62) of the present embodiment is open, although a transparent lens could be used to cover the display window (62) to prevent the ingress of dirt, dust, liquid, etc., into the mechanism and/or act as a magnifier.

The counter ring (30) is engaged with the dose setting dial (22) by means of a plurality of rib grooves (64) formed on the outer circumference of the dose setting dial (22) from its distal end to its proximal end, and a corresponding number of ribs (63) formed on the inner surface of the counter ring (30). The counter ring (30) can move axially towards both the proximal end and distal end of the dose setting dial (22). To prevent axial movement of the counter ring (30) with respect to the dose setting dial (22), a positioning collar (65) is assembled on the outer circumference of the dose setting dial (22) and secured to the inner surface of the housing (2) adjacent to the proximal end of the counter ring (30). A cylindrical positioning collar (65), integrated into the housing (2), abuts the distal end of the counter ring (30). Thus the counter ring (30) is able to rotate with the dose setting dial (22) with respect to the housing during dose setting and dose delivery, but is prevented from axial movement with respect to the housing (2).

In the present embodiment the counter ring (30) displays the "unit" values for the set dose from "0" to "9". The "tens" values are indicated on the dose setting dial (22) such that during on complete revolution of the counter ring (30) the corresponding "tens" value is continuously displayed.

All three screw structures in the device according to instant invention (i.e., 35, 44, and 47) have differing screw pitches. The ratio in the screw pitches between the first (35), the second (44), and the third screw structure (47) is about 3:2:1, in order to achieve an efficient reduction of transmission forces ("speed reduction") of the screw structures.

Embodiment 2 of the device (1) is described with reference to FIGS. 7 and 8.

The present embodiment 2 includes a modification to the first clutch (56), between the dose setting dial (22) and the inner cylinder (23).

Figure 7:
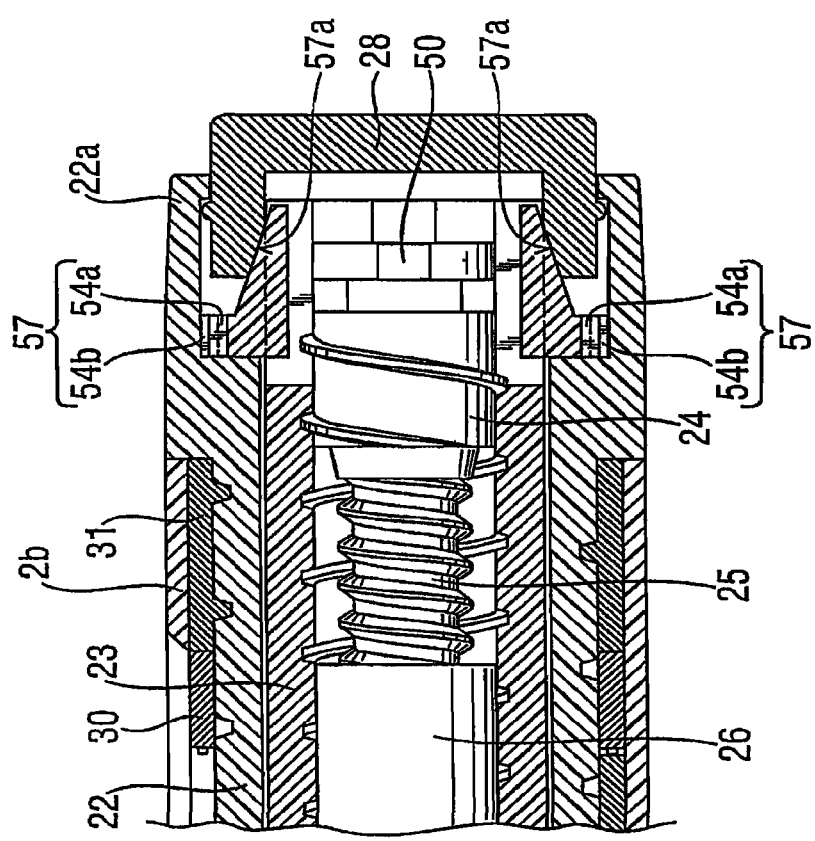
FIG. 7 is a sectional side view showing the device in a clutched state.
Figure 8:
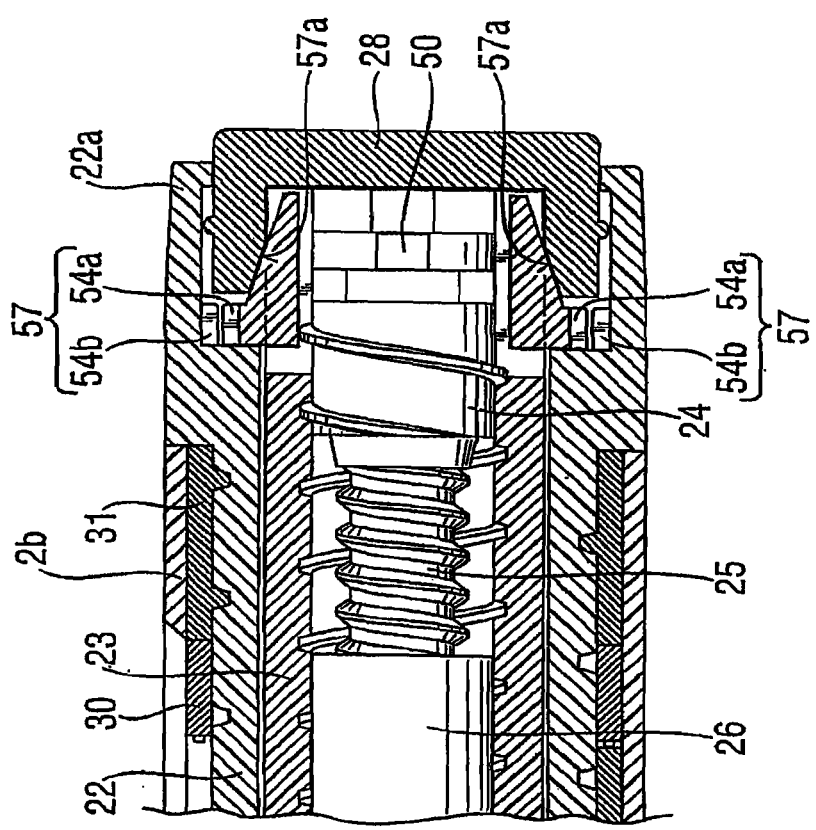
FIG. 8 is a sectional side view showing the device in a declutched state.

FIG. 7 indicates an alternative clutch (57) that is located at the proximal end of the inner cylinder (23). The clutch (57) consists of conical cam faces (57a) and a plurality of equidistantly spaced first engaging portions (54a). Through the axial movement of the release knob (28) either towards the distal end or towards the proximal end, the clutch (57) can be compressed or expanded to cause the first engaging portions (54a) to engage with or disengage from the corresponding second engaging portion (54b) formed on the inner face of the rotating knob (22a). The first engaging portions (54a) and the second engaging portion (54b) are engaged, e.g., by the spring force of a pair of spring acting portions (not shown).

During dose setting, the first engaging portions (54a) and second engaging portion (54b) are engaged under the spring force thus coupling the inner cylinder (23) with the dose setting dial (22) and preventing relative rotation between the inner cylinder (23) and the dose setting dial (22).

During dose dispensing, the release knob (28) is pushed in the distal direction disengaging the first engaging portions (54a) from the second engaging portion (54b) thereby disconnecting the dose setting dial (22) from the inner cylinder (23) and allowing the dose setting dial (22) to rotate with respect to the inner cylinder (23).

Figure 9:
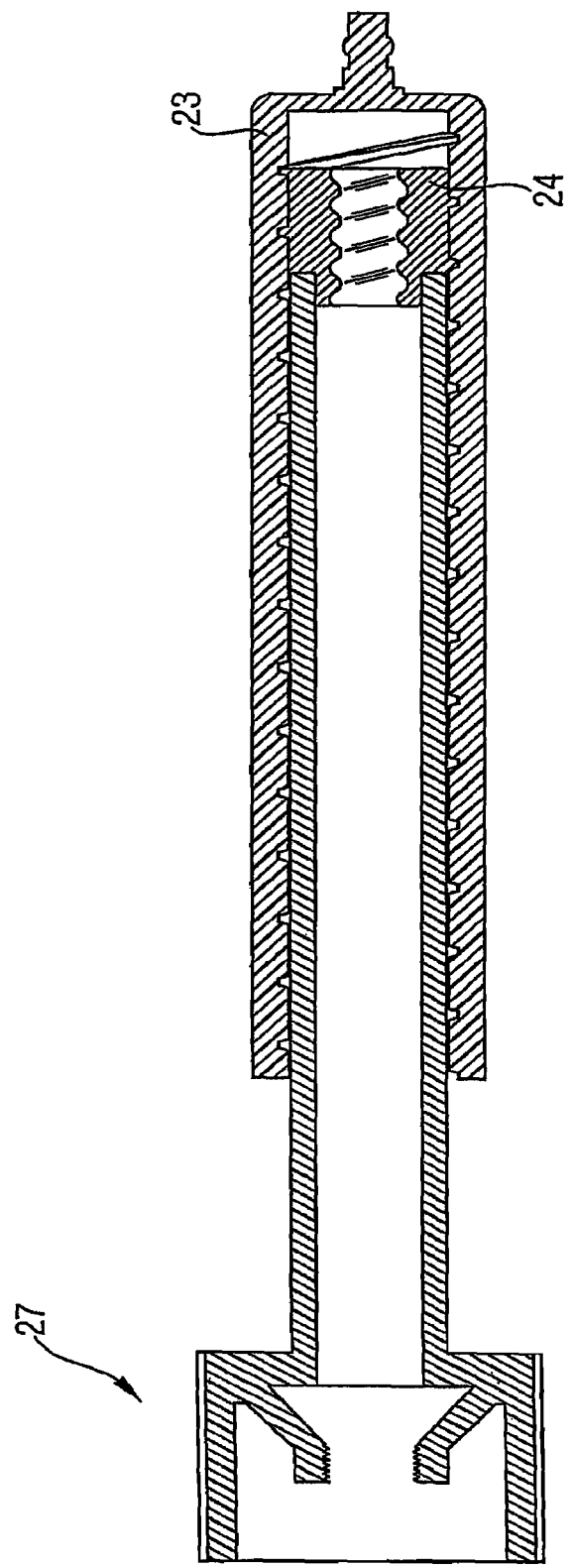
FIG. 9 is a sectional side view showing an alternative of the free lock.

The mechanism and the device of the present invention is not limited to the embodiments 1 and 2 described above but allows various effective alterations based on the technical idea of the present invention. For example, FIG. 9 shows an alternative solution, wherein the free lock is fixed to the plunger rod holder.

In this case, the screw pitch ratios between the $1^{st}$, $2^{nd}$ and $3^{rd}$ screw structures are about 3:3:1.

The invention claimed is:

1. A drive mechanism for use in a drug delivery device comprising:
    a first member having a proximal end, a distal end and an internal thread;
    a second member threadedly engaged with the internal thread and configured to simultaneously rotate and traverse axially towards the proximal end during dose setting and to simultaneously rotate and traverse axially towards the distal end during dose dispensing;
    a third member rotatably fixed relative to the first member during both dose setting and dose dispensing, the third member having a threaded hollow portion;
    a fourth member threadedly engaged with the threaded hollow portion such that the fourth member can rotate relative to the third member;
    a fifth member engaged with and positioned within the second member such that axial movement of the second member causes simultaneous axial movement of the fifth member, where the fifth member is rotatably fixed relative the fourth member; and
    a sixth member rotatably fixed relative to the first member and configured to prevent the third member from rotating during dose setting, where during dose dispensing the sixth member allows the third member to move axially towards the distal end.

2. The drive mechanism according to claim 1 further comprising a cylindrical rotating knob rotatably fixed relative to the second member.

3. A drug delivery device comprising the drive mechanism according to claim 2.

4. The drive mechanism according to claim 1 further comprising a release knob configured to move axially and distally during dose dispensing to cause the second member and fifth member to simultaneously move distally.

5. A drug delivery device comprising the drive mechanism according to claim 4.

6. The drive mechanism according to claim 1 further characterized in that rotational movement of the third member is prevented by a non-circular keyed connection with an internal portion in the sixth member.

7. A drug delivery device comprising the drive mechanism according to claim 6.

8. A drug delivery device comprising the drive mechanism according to claim 1.

9. A drug delivery device according to claim 8 containing insulin, heparin, or a derivative or analogue thereof.

10. A method of delivering a pharmaceutical formulation to a human or animal body comprising administering the pharmaceutical formulation from a drug delivery device according to claim 8.

11. A method of delivering a pharmaceutical formulation to a human or animal body comprising administering the pharmaceutical formulation from a drug delivery device comprising the drive mechanism according to claim 1.

12. A method according to claim 11 wherein the pharmaceutical formulation contains insulin, heparin, a derivative thereof or an analogue thereof.

13. A method of assembling a drug delivery device comprising a drive mechanism according to claim 1, comprising mounting the drive mechanism to any other components of the drug delivery device.

14. The drive mechanism according to claim 1 where the first member is a housing.

15. The drive mechanism according to claim 1 where the second member is a dose setting member.

16. The drive mechanism according to claim 1 where the third member is a plunger rod.

17. The drive mechanism according to claim 1 where the fourth member is a lead screw.

18. The drive mechanism according to claim 1 where the fifth member is a inner cylinder.

19. The drive mechanism according to claim 1 where the sixth member is a plunger rod holder.

20. A drive mechanism for use in a drug delivery device comprising:
    a housing having a proximal end, a distal end and an internal thread;
    a dose setting dial threadedly engaged with the internal thread and configured to simultaneously rotate and traverse axially towards the proximal end during dose setting and to simultaneously rotate and traverse axially towards the distal end during dose dispensing;
    a plunger rod rotatably fixed relative to the housing during both dose setting and dose dispensing, the plunger rod having a threaded hollow portion;
    a lead screw threadedly engaged with the threaded hollow portion such that the lead screw can rotate relative to the plunger rod;
    an inner cylinder engaged with and positioned within the dose setting dial such that axial movement of the dose setting dial causes simultaneous axial movement of the inner cylinder, where the inner cylinder is rotatably fixed relative the lead screw; and
    a plunger rod holder rotatably fixed relative to the housing and configured to prevent the plunger rod from rotating during dose setting, where during dose dispensing the plunger rod holder allows the plunger rod to move axially towards the distal end.

* * * * *